US 008362425B2

(12) United States Patent
Han et al.

(10) Patent No.: US 8,362,425 B2
(45) Date of Patent: Jan. 29, 2013

(54) MULTIPLE-BEAM SYSTEM FOR HIGH-SPEED ELECTRON-BEAM INSPECTION

(75) Inventors: Liqun Han, Pleasanton, CA (US); Xinrong Jiang, Palo Alto, CA (US); John D. Greene, Santa Cruz, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/095,585

(22) Filed: Apr. 27, 2011

(65) Prior Publication Data

US 2012/0241606 A1    Sep. 27, 2012

Related U.S. Application Data

(60) Provisional application No. 61/466,466, filed on Mar. 23, 2011.

(51) Int. Cl.
*G01N 23/04* (2006.01)
*G01N 23/00* (2006.01)

(52) U.S. Cl. .................. 250/307; 250/306; 250/310

(58) Field of Classification Search .................. 250/306, 250/307, 310, 396 R, 397, 398, 399, 492.1, 250/492.22, 492.23, 492.24, 492.3, 526
See application file for complete search history.

(56) References Cited

U.S. PATENT DOCUMENTS

| | | | |
|---|---|---|---|
| 3,930,181 A | 12/1975 | Pfeiffer | |
| 3,984,687 A | 10/1976 | Loeffler et al. | |
| 4,084,095 A | 4/1978 | Wolfe | |
| 6,011,269 A | 1/2000 | Veneklasen et al. | |
| 6,448,568 B1 | 9/2002 | Allen et al. | |
| 6,897,458 B2 * | 5/2005 | Wieland et al. | 250/494.1 |
| 7,091,504 B2 * | 8/2006 | Wieland et al. | 250/494.1 |
| 7,109,486 B1 | 9/2006 | Spallas et al. | |
| 7,420,164 B2 * | 9/2008 | Nakasuji et al. | 250/307 |
| 7,427,765 B2 | 9/2008 | Buller et al. | |
| 7,633,069 B2 | 12/2009 | Rafferty | |
| 7,800,075 B2 | 9/2010 | Buller et al. | |
| 7,821,187 B1 | 10/2010 | Jiang et al. | |
| 2002/0148971 A1 | 10/2002 | Sogard | |
| 2003/0085353 A1 * | 5/2003 | Almogy et al. | 250/310 |
| 2005/0263715 A1 * | 12/2005 | Nakasuji et al. | 250/396 ML |
| 2007/0085033 A1 | 4/2007 | Buller et al. | |
| 2008/0093561 A1 | 4/2008 | Rafferty | |
| 2008/0174771 A1 * | 7/2008 | Yan et al. | 356/237.5 |
| 2008/0308751 A1 | 12/2008 | Buller et al. | |
| 2008/0315090 A1 * | 12/2008 | Nakasuji et al. | 250/306 |
| 2009/0309022 A1 * | 12/2009 | Gunji et al. | 250/307 |
| 2012/0241641 A1 * | 9/2012 | Sano et al. | 250/396 R |

FOREIGN PATENT DOCUMENTS

JP    10-062149 A    3/1998

OTHER PUBLICATIONS

PCT International Search Report & Written Opinion for Application No. PCT/US2012/028336, Oct. 8, 2012, 8 sheets.

* cited by examiner

*Primary Examiner* — Bernard E Souw
(74) *Attorney, Agent, or Firm* — Okamoto & Benedicto LLP

(57) ABSTRACT

One embodiment disclosed relates to a multiple-beamlet electron beam imaging apparatus for imaging a surface of a target substrate. A beam splitter lens array is configured to split the illumination beam to form a primary beamlet array, and a scanning system is configured to scan the primary beamlet array over an area of the surface of the target substrate. In addition, a detection system configured to detect individual secondary electron beamlets. Another embodiment disclosed relates to a method of imaging a surface of a target substrate using a multiple-beamlet electron beam column. Other features and embodiments are also disclosed.

19 Claims, 12 Drawing Sheets

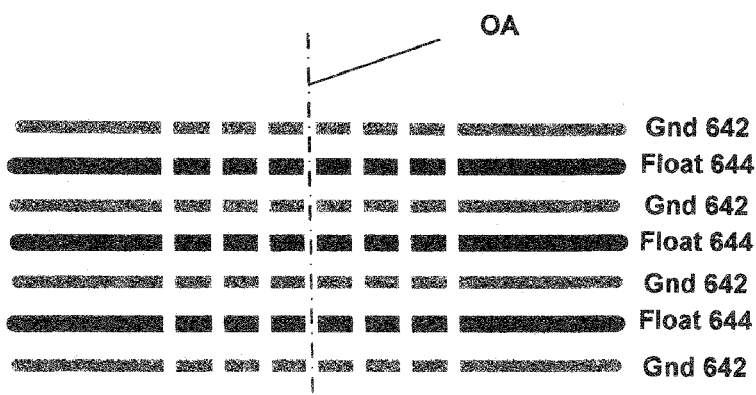
FIG. 6B  (Cross-sectional view)
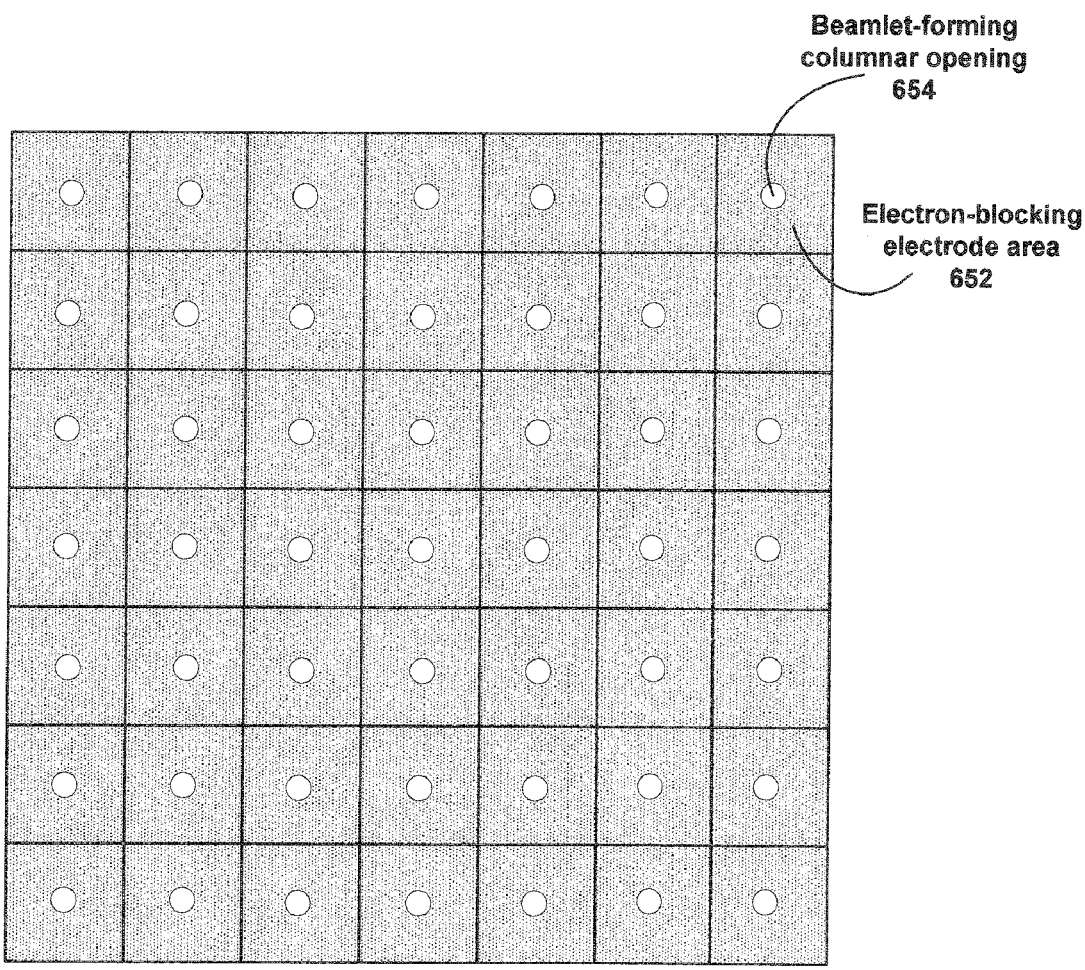
FIG. 6C  (Plan View)

MULTIPLE-BEAM SYSTEM FOR HIGH-SPEED ELECTRON-BEAM INSPECTION

CROSS-REFERENCE TO RELATED APPLICATION(S)

The present application claims the benefit of US. Provisional Application No. 61/466,466, filed on Mar. 23, 2011, entitled "Multiple-Beam System for High-Speed E-Beam Inspection," the disclosure of which is hereby incorporated by reference.

BACKGROUND

1. Technical Field

The present invention relates to apparatus and methods for automated inspection of manufactured substrates.

2. Description of the Background Art

Automated electron beam inspection systems typically use an electron beam column to scan an electron beam across a region of a substrate surface to obtain image data. The image data may be processed to detect manufacturing defects in the region.

BRIEF DESCRIPTION OF THE DRAWINGS

FIG. 6B is a cross-sectional diagram showing a beam splitter electrostatic lens array stack in accordance with an embodiment of the invention.

FIG. 6C is a plan view diagram showing a beam splitter electrostatic lens array stack in accordance with an embodiment of the invention.

SUMMARY

One embodiment disclosed relates to a multiple-beamlet electron beam imaging apparatus for imaging a surface of a target substrate. A beam splitter lens array is configured to split the illumination beam to form a primary beamlet array, and a scanning system is configured to scan the primary beamlet array over an area of the surface of the target substrate. In addition, a detection system configured to detect individual secondary electron beamlets. Another embodiment disclosed relates to a method of imaging a surface of a target substrate using a multiple-beamlet electron beam column. Other embodiments, aspects and feature are also disclosed.

DETAILED DESCRIPTION

Conventional systems for wafer and reticle inspection raster scan a single beam over a sample area and obtain image data pixel by pixel. This results in a very slow speed (low throughput) for conventional inspection systems.

In contrast to conventional systems, the present disclosure provides a novel and inventive multiple-beam system for use in automated electron beam inspection and other applications. The system, apparatus, and methods disclosed herein may be advantageously applied, for example, to defect inspection of semiconductor wafers, reticles, photo masks, EUV masks, and other manufactured substrates.

Figure 1:
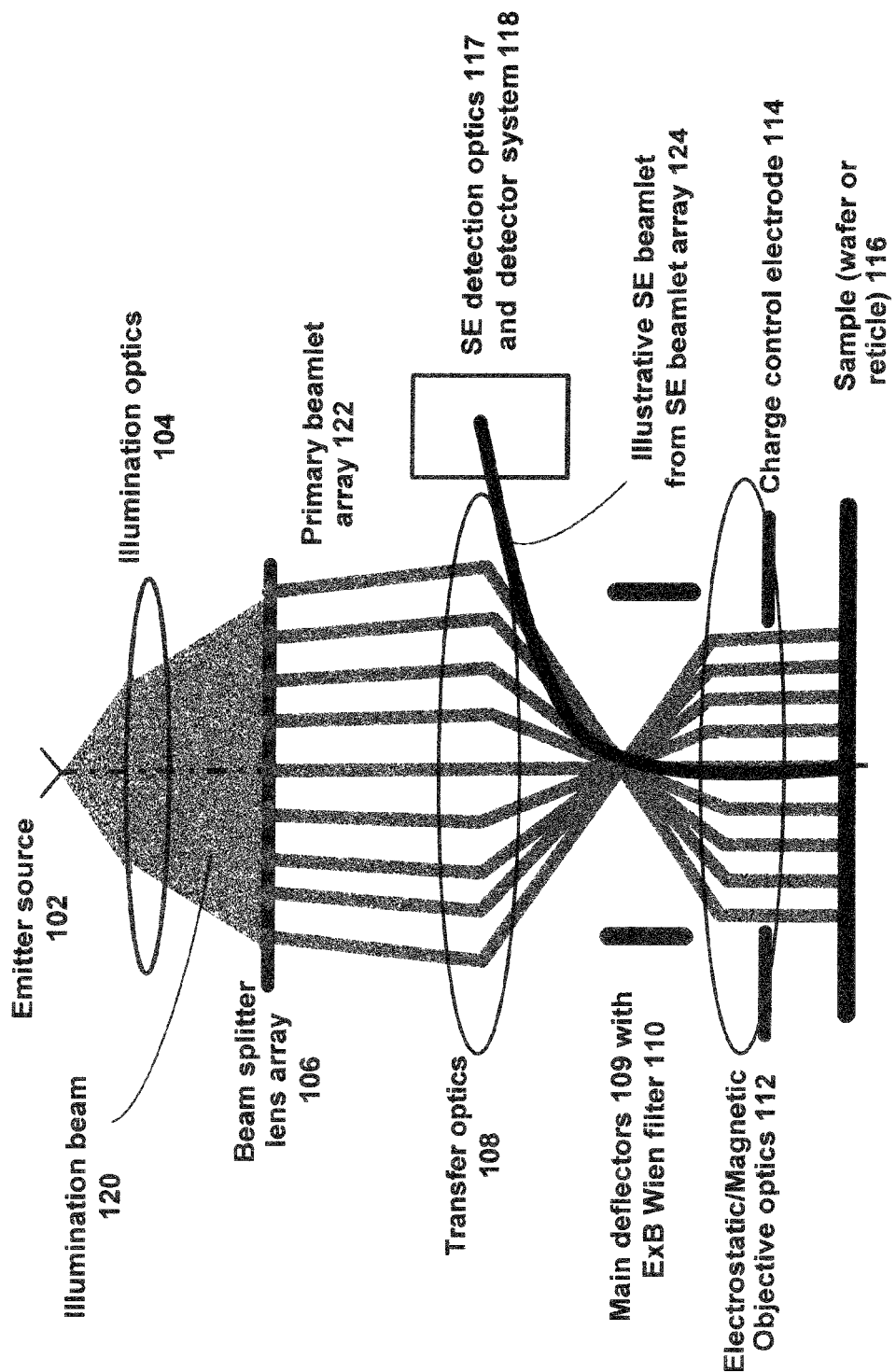
FIG. 1 is a cross-sectional diagram depicting electron-optics of a multi-beam electron beam column for an automated inspection system in accordance with an embodiment of the invention.

FIG. 1 is a cross-sectional diagram depicting electron-optics of a multi-beam electron beam (e-beam) column 100 for an automated inspection system in accordance with an embodiment of the invention. The multi-beam e-beam column 100 shown in FIG. 1 produces multiple beamlets from a single electron emitter and shares column optical elements by the beamlets. As depicted, the multi-beam electron beam column 100 includes an emitter source 102, illumination electron-optics (illumination optics) 104, a beam splitter lens array 106, transfer electron-optics (transfer optics) 108, main deflectors 109 with an ExB Wien filter 110, electrostatic and/or magnetic objective optics 112, charge control electrode 114, a sample (wafer or reticle) 116 being imaged, and secondary electron detection electron-optics (SE detection optics) 117 and a detector system 118.

The emitter source 102 may be implemented as a Schottky tip and is configured to emit electrons for the illumination beam 120. The illumination optics 104 may be configured to provide focus adjustment prior to the illumination beam 120 impinging upon the beam splitter lens array 106.

Multiple beamlets in a primary beamlet array 122 are formed by the electrons of the illumination beam 120 passing through the beam splitter lens array 106. For example, the primary beamlet array 122 may comprise twenty-five beamlets in a 5×5 array. More generally, it is contemplated that the number of beamlets in the primary beamlet array 122 may range from two to two hundred (2 to 200). Each beamlet in the primary beamlet array 122 has its own separate virtual source. The primary beamlet array 122 is further focused by the transfer and objective optics (108 and 112) to multiple beamlet spots on the surface of the sample 116. The build-up of charge on the surface of the sample 116 may be controlled using the charge control electrode 114.

The main deflectors 109 may be configured to scan the primary beamlet array 122 over an area of the sample 116.

Each beamlet spot on the surface of the sample 116 generates a corresponding secondary electron (SE) beamlet. An array of SE beamlets 124 is generated due to the impingement of the primary beamlet array 122 onto the surface of the sample 116. In FIG. 1, one illustrative SE beamlet of the array of SE beamlets 124 is shown.

The ExB Wien filter 110 may be configured to separate the SE beamlet array 124 from the primary beamlet array 122 by bending the upwards trajectories of the SE beamlets towards the SE detection optics 117 (while not bending the downwards trajectories of the primary beamlets). The SE detection optics 117 may be configured to focus each SE beamlet onto a detector element of the detector system 118. As such, signal electrons from each SE beamlet in the array 124 may be detected in parallel by multiple detector elements in the detector system 118.

Figure 2:
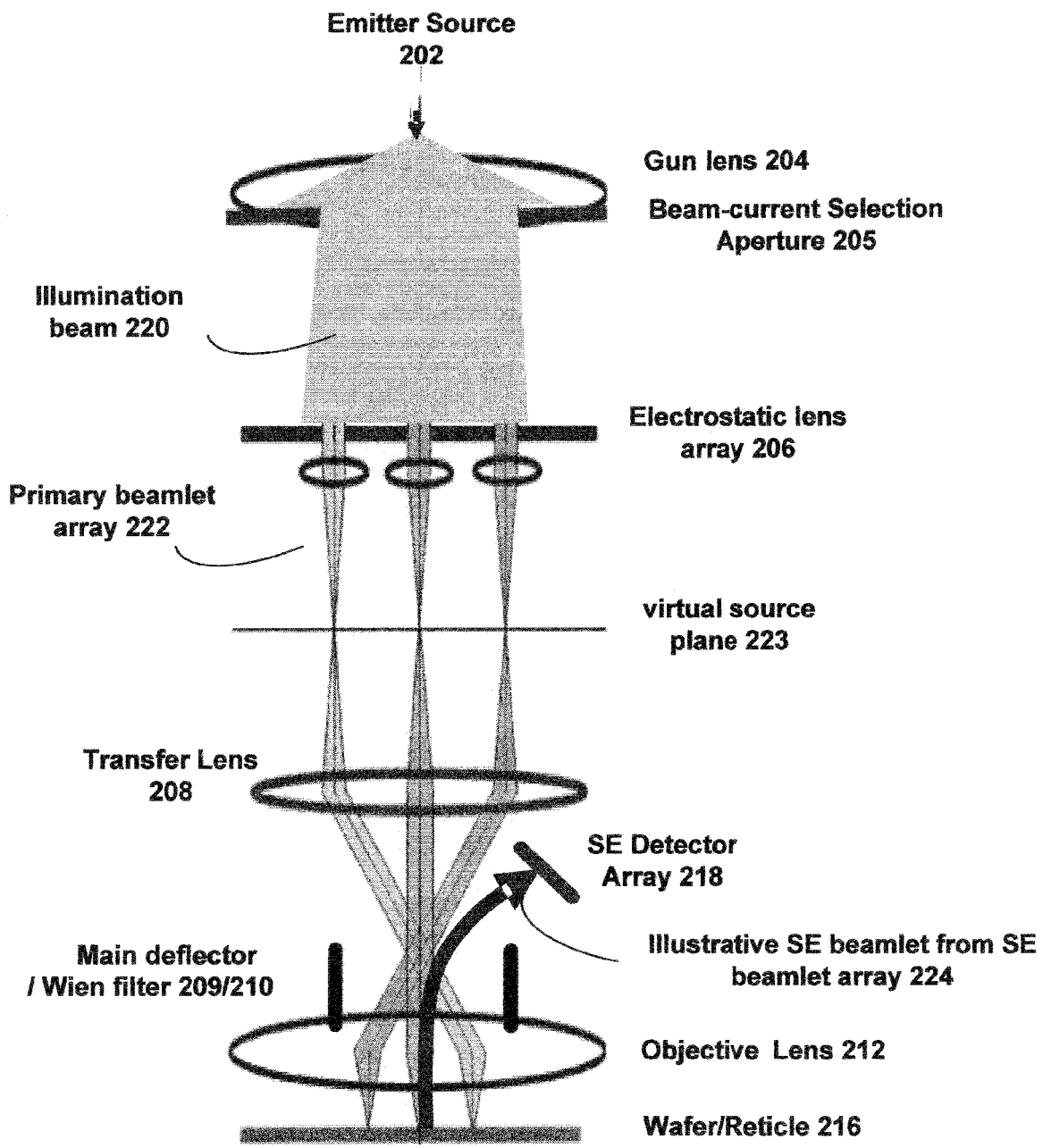
FIG. 2 is a cross-sectional diagram of a first configuration of select electron-optical components in accordance with an embodiment of the invention.

FIG. 2 is a cross-sectional diagram of a first configuration 200 of select electron-optical components in accordance with an embodiment of the invention. Components shown in FIG. 2 include an emitter source 202, a gun lens 204, a beam-current selection aperture 205, an electrostatic lens array 206, transfer lens 208, main deflector 209/Wien filter 210, objective lens 212, a substrate (wafer or reticle) 216 being imaged, and secondary electron (SE) detector array 218.

As shown, the illumination system includes an emitter source 202, a gun lens 204, and a beam-current selection aperture 205. The emitter source 202 emits electrons which are focused by the gun lens 204 and limited by the beam-current selection aperture 205 so as to generate the illumination beam 220.

Multiple beamlets in a primary beamlet array 222 are formed by the electrons of the illumination beam 220 passing through the electrostatic lens array 206. For example, the primary beamlet array 222 may comprise nine beamlets in a 3×3 array. More generally, it is contemplated that the number of beamlets in the primary beamlet array 222 may range from two to two hundred (2 to 200). Each beamlet in the primary beamlet array 222 has its own separate virtual source located on the virtual source plane 223. The primary beamlet array 222 is further focused by the transfer and objective optics (208 and 212) to multiple beamlet spots on the surface of the sample 216.

The main deflector 209 may be configured to scan the primary beamlet array 222 over an area of the sample 216. Each beamlet spot on the surface of the sample 216 generates a corresponding secondary electron (SE) beamlet. An array of SE beamlets 224 is generated due to the impingement of the primary beamlet array 222 onto the surface of the sample 216. In FIG. 1, one illustrative SE beamlet of the array of SE beamlets 224 is shown.

The ExB Wien filter 210 may be configured to separate the SE beamlet array 224 from the primary beamlet array 222 by bending the upwards trajectories of the SE beamlets towards the SE detector array 218 (while not bending the downwards trajectories of the primary beamlets). In the configuration depicted in FIG. 2, the SE detector array 218 is positioned just following the Wien filter 210. This detection arrangement is advantageously compact.

Figure 3:
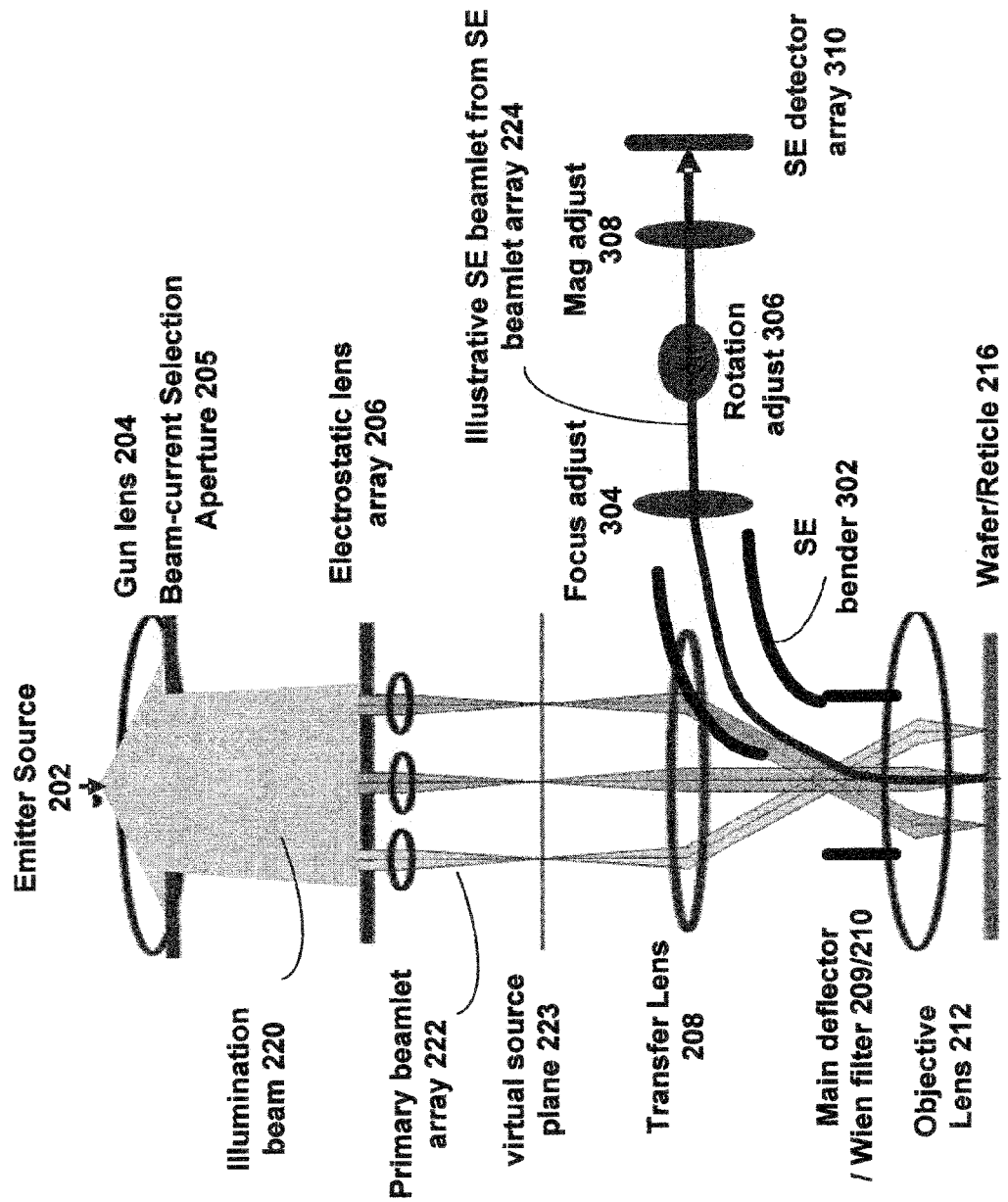
FIG. 3 is a cross-sectional diagram of a second configuration of select electron-optical components in accordance with an embodiment of the invention.

FIG. 3 is a cross-sectional diagram of a second configuration 300 of select electron-optical components in accordance with an embodiment of the invention. This configuration 300 has a different detection arrangement compared to the first configuration 200 of FIG. 2.

In the detection arrangement shown in FIG. 3, the SE beamlet array 224 is bent further away from the primary beamlet array 222 using an SE bender 302. This provides space for additional electron-optical components to adjust the SE beamlet array 224 prior to the SE beamlet array 224 reaching the SE detector array 310. For example, the additional components may include, in series, a variable focus adjustment electron lens (focus adjust) 304, a variable rotation adjustment electron lens (rotation adjust) 306, and a variable magnification adjustment electron lens (mag adjust) 308. Advantageously, this detection arrangement may provide superior multi-beam imaging detection quality and flexibility.

Figure 4A:
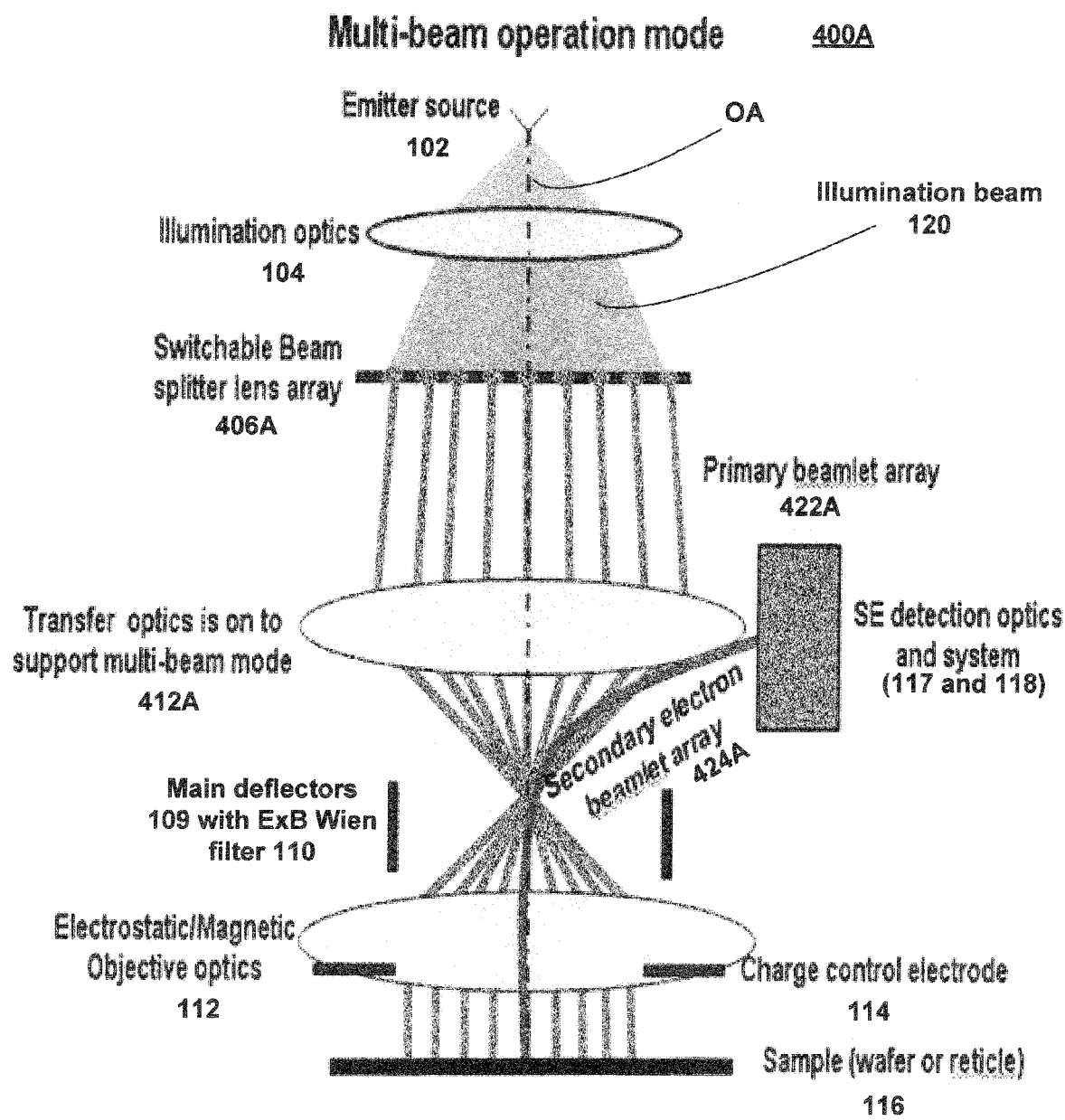
FIGS. 4A and 4B are cross-sectional diagrams which illustrate switchability between multi-beam and single-beam operational modes in accordance with an embodiment of the invention.
Figure 4B:
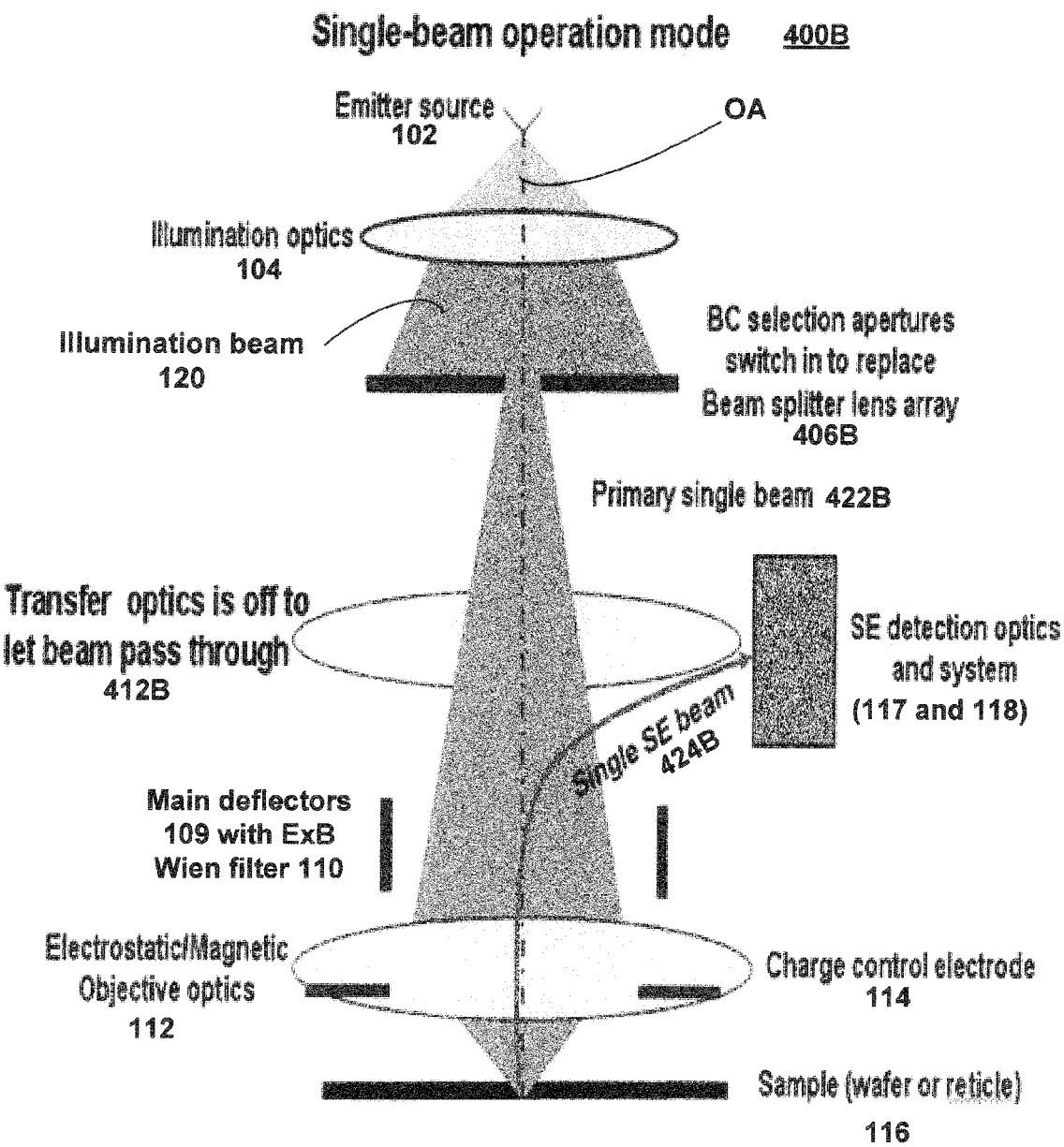

FIGS. 4A and 4B are cross-sectional diagrams which illustrate switchability between multi-beam and single-beam operational modes in a single electron beam column in accordance with an embodiment of the invention. FIG. 4A shows the electron-optics of a multi-beam e-beam column when it is operating in a multi-beam mode 400A, while FIG. 4B shows the electron-optics of a multi-beam e-beam column when it is operating in a single-beam mode 400B.

In FIG. 4A, the switchable beam splitter lens array 406A is in place such that the illumination beam 120 is split into a primary beamlet array 422A. In addition, the transfer optics is turned on 412A to support the multi-beam mode. As such, the primary beamlet array 422A impinges upon an array of spots on the surface of the sample 116 and results in the secondary electron beamlet array 424A which is detected by the SE detection optics and system (117 and 118).

In FIG. 4B, one of a plurality of beam-current (BC) selection apertures 406B are switched into place (replacing the beam splitter lens array 406A). This results in a primary single beam 422B (instead of a primary beamlet array 422A). In addition, the transfer optics is turned off 412B to allow the primary single beam 422B to pass through. Hence, the primary single beam 422B impinges upon a single spot on the surface of the sample 116 and results in the single secondary electron (SE) beam 424B (instead of the SE beamlet array 424A) which is detected by the SE detection optics and system (117 and 118).

Figure 5:
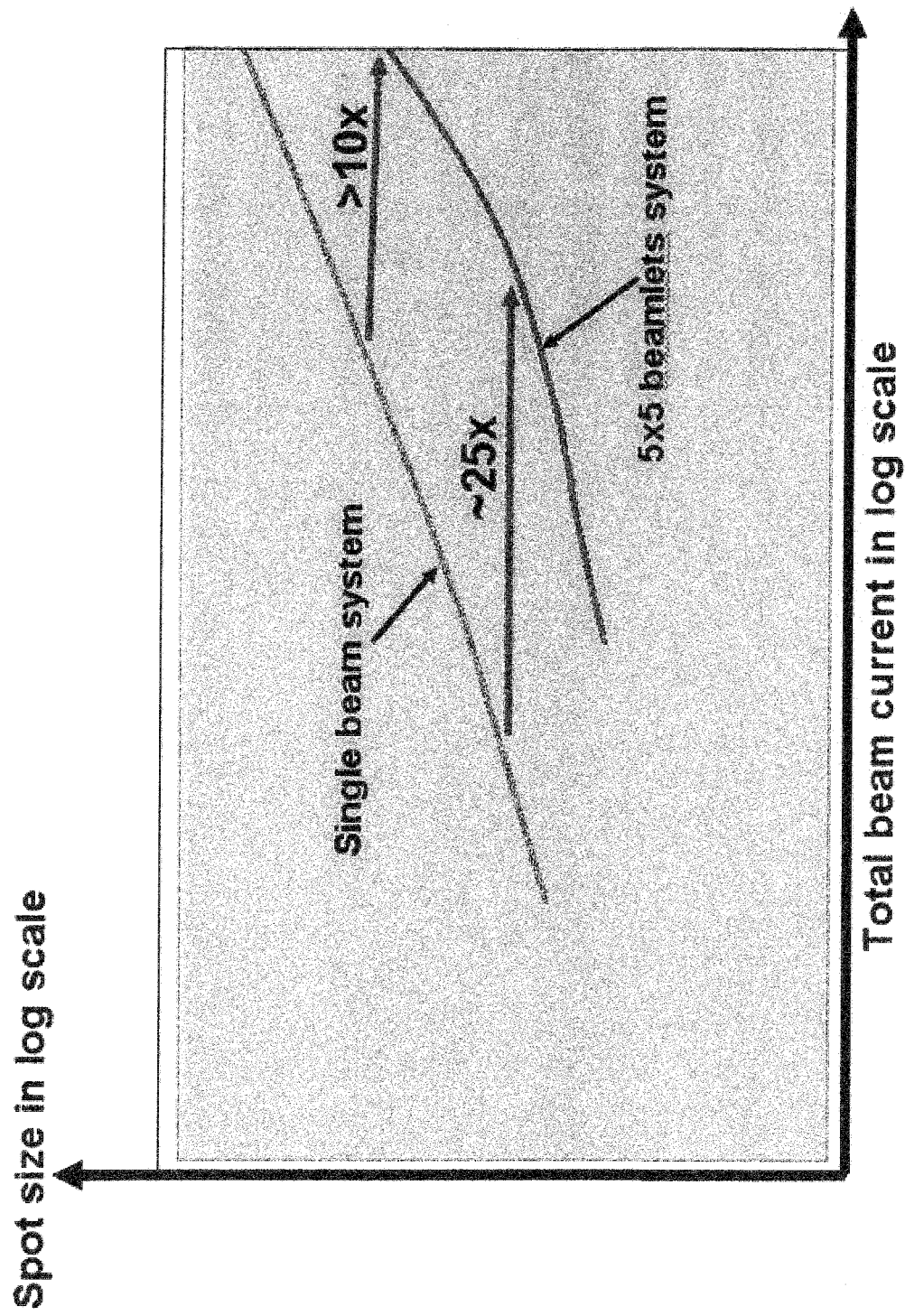
FIG. 5 is a graph showing beam current improvement which is achieved in accordance with an embodiment of the invention.

FIG. 5 is a graph showing beam current improvement which is achieved in accordance with an embodiment of the invention. The graph shows beam spot size (in log scale) on the vertical axis and total beam current (in log scale) on the horizontal axis. Computed curves from electron-optical simulations are shown for a single beam system 502 and for a system with 25 beamlets in a 5×5 array 504. For the same spot size (i.e. for the same resolution capability), the 5×5 beamlet system is shown to provide a total beam current which is more than ten times (10×) and up to about twenty-five (25×) times that of the single beam system.

Figure 6A:
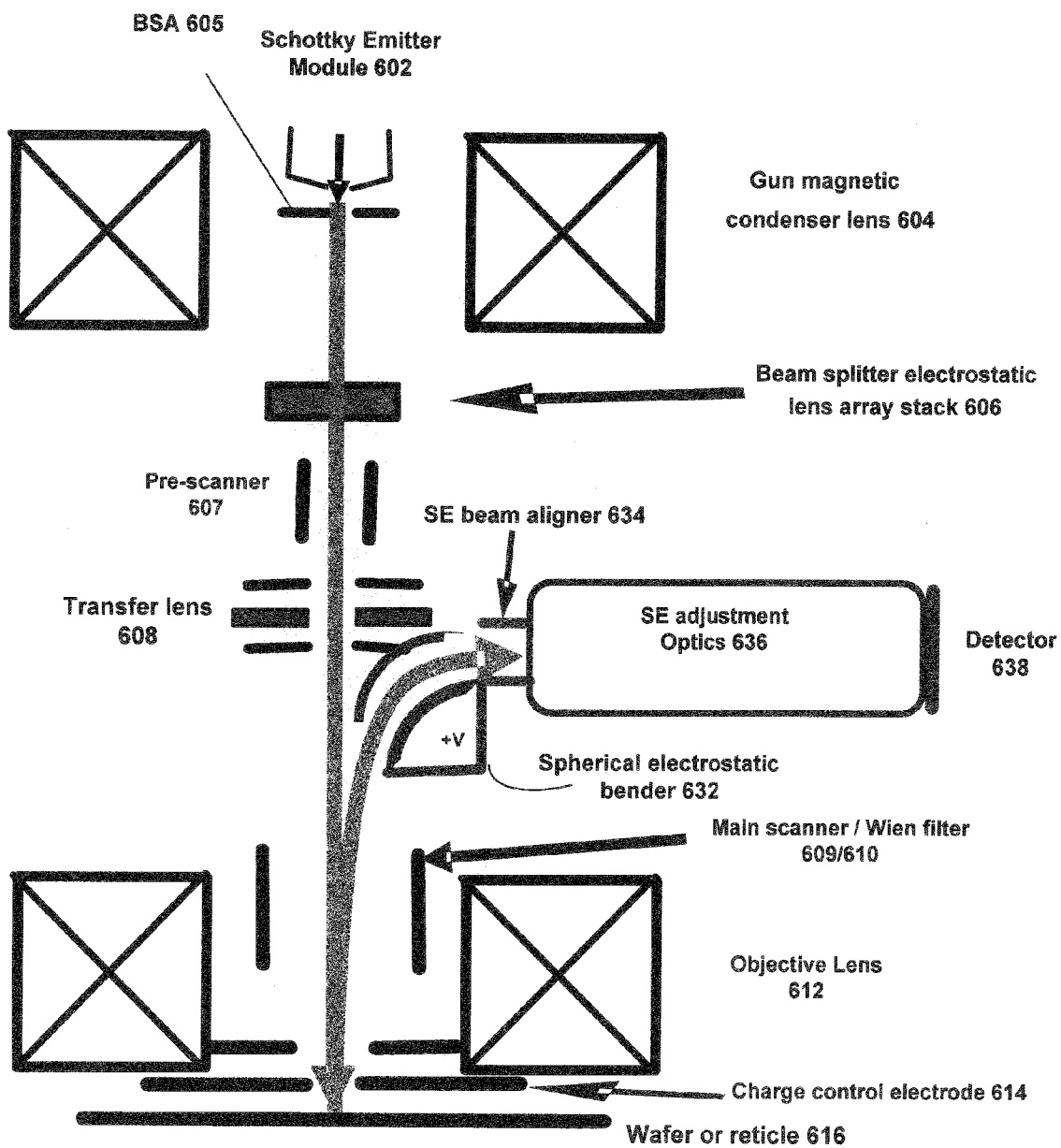
FIG. 6A is a cross-sectional diagram depicting an implementation of a multi-beam electron beam column for an automated inspection system in accordance with an embodiment of the invention.

FIG. 6A is a cross-sectional diagram depicting an implementation of a multi-beam electron beam column 600 for an automated inspection system in accordance with an embodiment of the invention. As shown, the multi-beam electron beam column 600 includes a Schottky emitter module 602, a gun magnetic condenser lens 604, a beam-current selection aperture (BSA) 605, a beam splitter electrostatic lens array stack 606, pre-scanner deflector 607, a three-electrode electrostatic transfer lens 608, main scanner deflector/Wien filter 609/610, an electro-magnetic objective optics 612, charge control electrode 614, and a sample (wafer or reticle) 616 being imaged.

In this implementation, the gun magnetic condenser lens may be an immersion magnetic condenser lens which may be configured to adjust the beam current density to illuminate the beam splitter. The beamlets in the primary beamlet array may be focused by the transfer lens to a common crossover at, or close to, the back-focal plane of the final objective lens. The electro-magnetic objective lens may be configured to focus the individual beamlets into individual spots on the sample surface. The primary beamlet array may be scanned over the sample surface using a scanning system which includes both the pre-scanner and the main scanner.

In addition, the multi-beam electron beam column 600 includes a spherical electrostatic bender 632 with a higher voltage (+V) on an inner spherical component so as to bend the secondary electron (SE) beamlet array to the SE beam aligner 634. The SE beam aligner 634 aligns the SE beamlet array so that the beamlets are properly aligned as they enter the SE adjustment optics 636. The SE adjustment optics 636 may be configured to adjust the focus, rotation, and magnification of the SE beamlet array so that the SE beamlets may be individually detected by cells or segments of the detector 638.

FIGS. 6B and 6C show, respectively, cross-section and plan views of a beam splitter electrostatic lens array stack 606 in further detail in accordance with an embodiment of the invention. The stack may include alternating electrically-grounded (gnd) electrode plates 642 and electrically-floating (float) electrode plates 644. In the illustrated example, there are seven plates, four grounded and three floating, with grounded plates being at the top and bottom of the stack. In this case, each electrostatic lens in the lens array may be considered to include three sets of three-electrode Enzel lenses. As contemplated herein, in other examples, the stack may have a different number of electrode plates.

The electrode plates are perforated with beamlet-forming columnar openings 654 which are aligned from plate to plate so as to extend through the stack. Each opening is surrounded by an electron-blocking electrode area 652. In the illustrated example, the openings form a 7×7 array so as to form a 7×7 array of primary beamlets. As contemplated herein, in other examples, the openings may be arranged so as to form other arrays beamlets (with the number of beamlets ranging from two to two hundred). A center such opening may be aligned with the optical axis (OA) of the electron beam column.

Figures 7A, 7B:
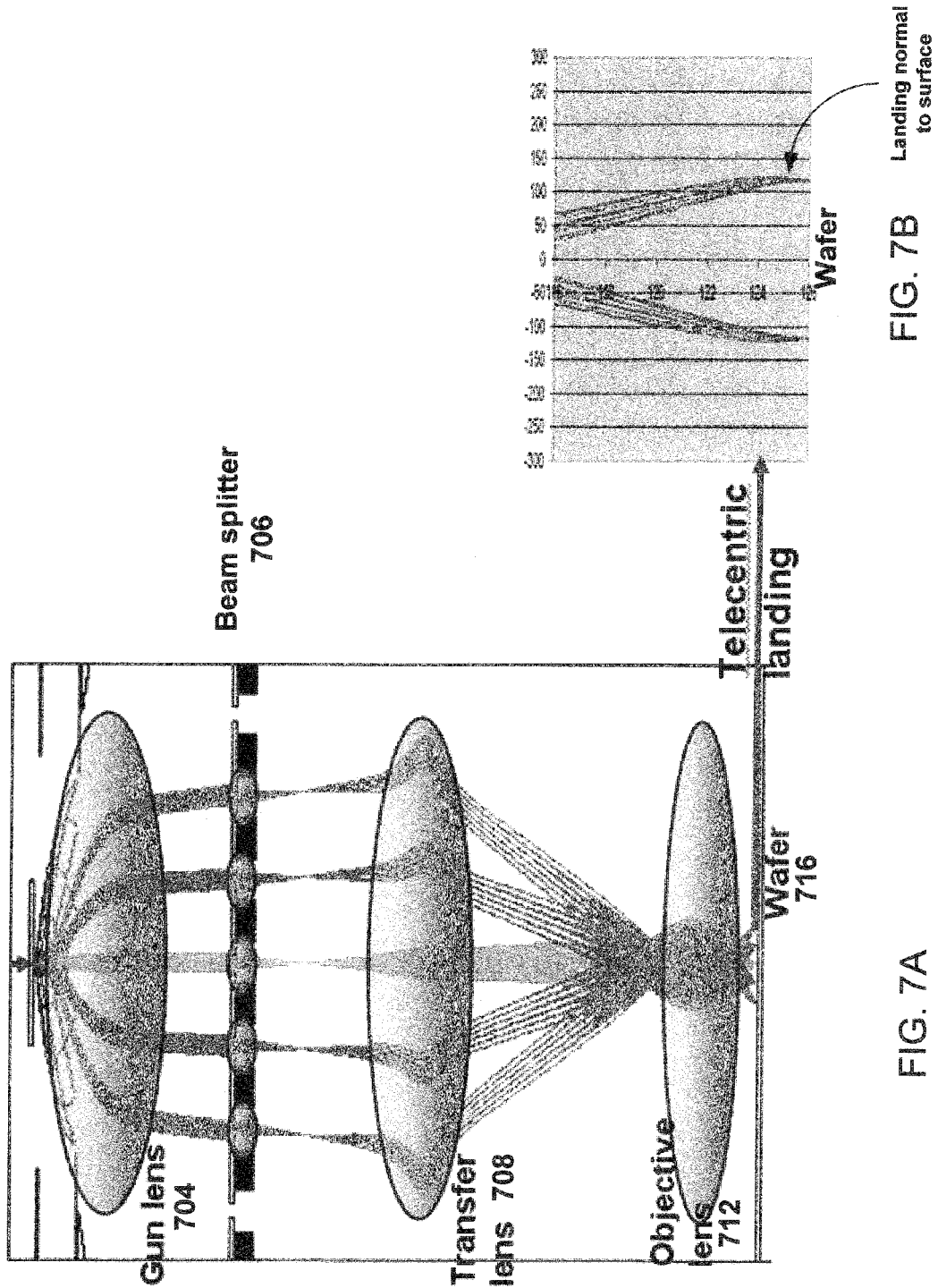
FIG. 7A is a cross-sectional diagram showing computer-simulated primary beam trajectories through the lenses of the multi-beam column in accordance with an embodiment of the invention.
FIG. 7B shows a close-up view of the computer-simulated primary electron trajectories as they impinge upon the surface of a wafer in accordance with an embodiment of the invention.

FIG. 7A is a cross-sectional diagram showing computer-simulated primary beam trajectories through the lenses of the multi-beam column in accordance with an embodiment of the invention. As shown, the lenses include the gun lens 704, the beam splitter lenses 706, the transfer lens 708, and the objective lens 712. FIG. 7B shows a close-up view of the computer-simulated primary electron trajectories as they impinge upon the surface of the wafer 716 in accordance with an embodiment of the invention. As sheen, the landing angle of the electrons is normal to the surface of the wafer. In other words, the primary electron beam has a telecentric landing at the target surface.

Figure 8:
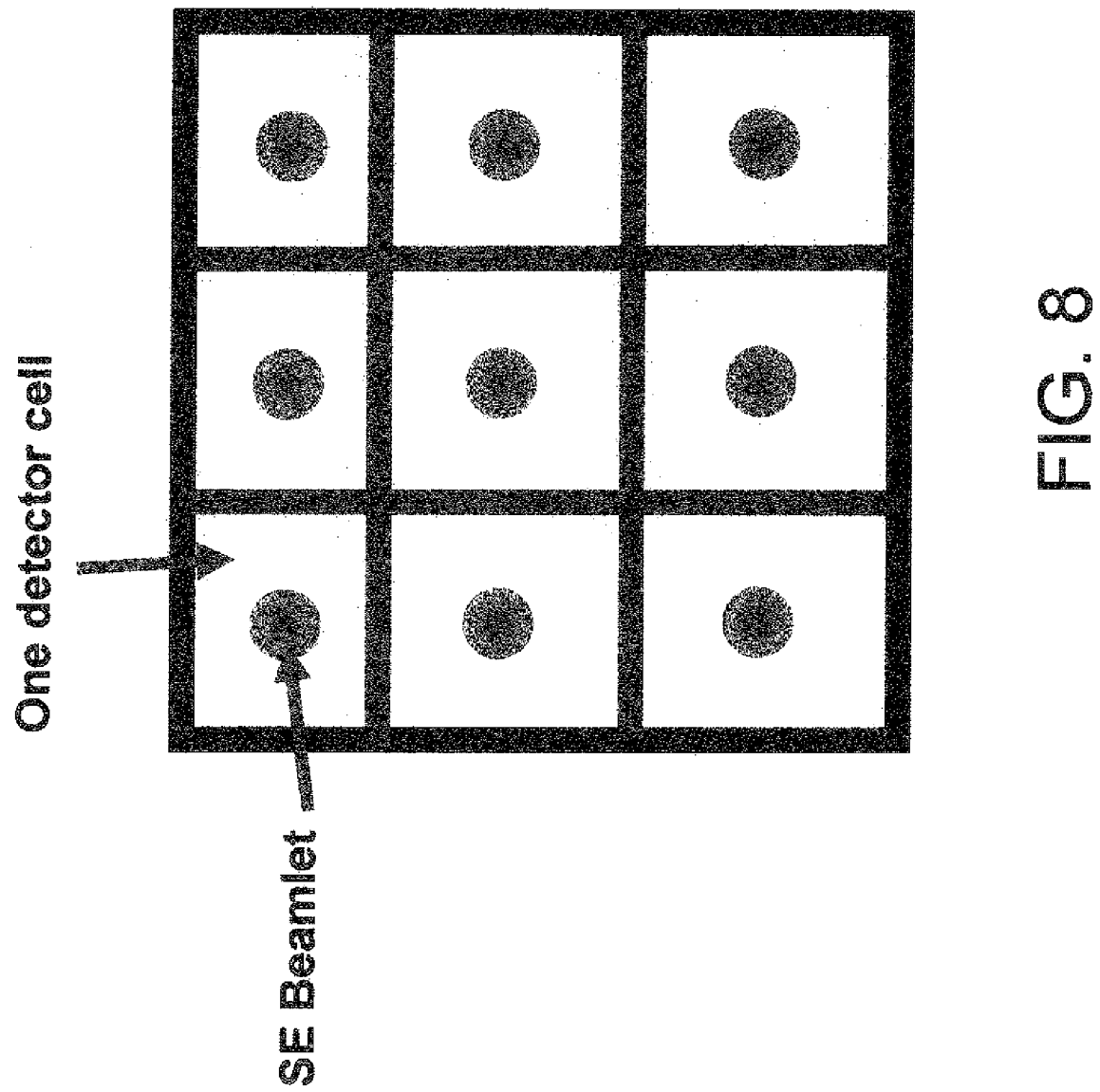
FIG. 8 is a plan view of a detector cell array in accordance with an embodiment of the invention.

FIG. 8 is a plan view of a detector cell array in accordance with an embodiment of the invention. As shown, the detector may include an array of detector cells, and each cell may detect a separate secondary electron (SE) beamlet.

While the illustrated example of a detector cell array in FIG. 8 shows nine detector cells in a 3×3 array, the number of cells in the detector array will depend on the particular implementation. In one embodiment, the number of cells in the detector array may correspond to the number of beamlets in the SE beamlet array to be detected. For example, if there are 25 SE beamlets in a 5×5 array, then there may be 25 detector cells in a 5×5 array to detect those SE beamlets.

Figure 9A:
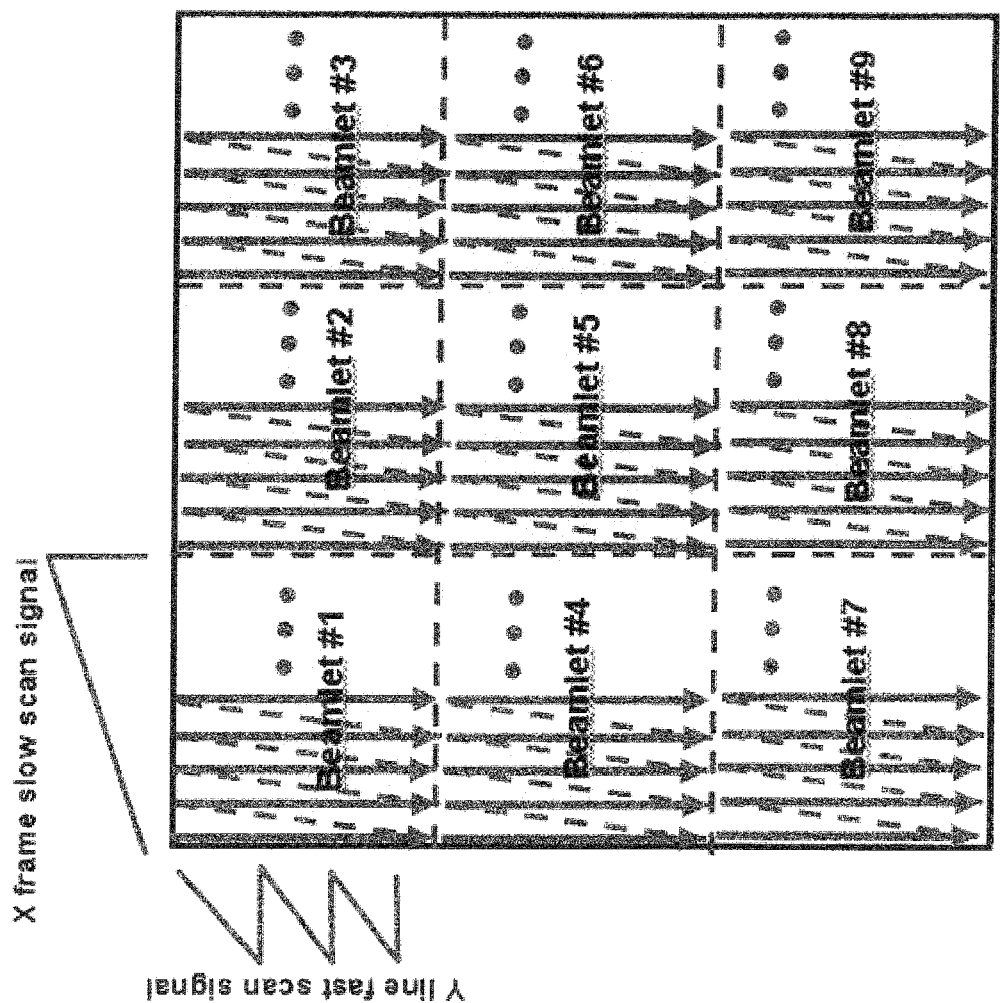
FIG. 9A is a schematic diagram depicting a frame image mode for beamlet scanning in accordance with an embodiment of the invention.
Figure 9B:
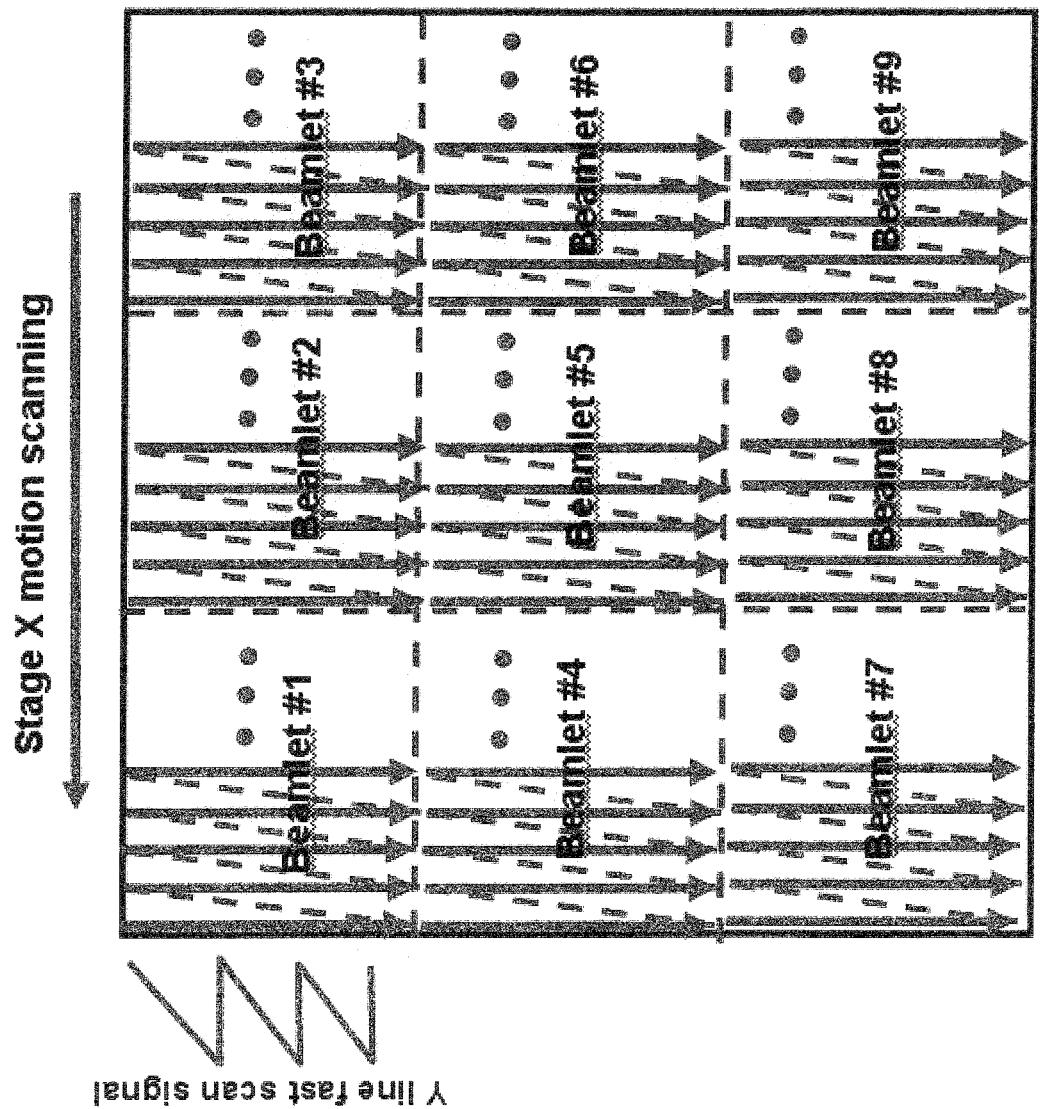
FIG. 9B is a schematic diagram depicting a swathing image mode for beamlet scanning in accordance with an embodiment of the invention.

As shown in FIGS. 9A and 9B, the beamlets of the primary beamlet array may be scanned simultaneously over individual regions of the sample surface. FIG. 9A is a schematic diagram depicting a frame image mode for beamlet scanning in accordance with an embodiment of the invention, while FIG. 9B is a schematic diagram depicting a swathing image mode for beamlet scanning in accordance with an embodiment of the invention.

In FIG. 9A, the sample may be stationary while the beamlets are scanned. Each beamlet may be scanned in a raster pattern such that it covers its own sub-area of the framed surface area to be scanned. For example, each beamlet may be controlled by a slower frame scan signal in the X-direction and a faster line scan signal in the Y-direction, where the period of the frame scan signal is multiple times longer than the period of the line scan signal. In this way, the entire framed surface area to be scanned may be imaged by the beamlet array.

In FIG. 9B, the sample is moving while the beamlets are scanned. In the example shown, the stage holding the sample is moving in a linear motion to the left in the X-direction. Meanwhile, each beamlet may be scanned using a line scan signal in the Y-direction. In this way, each beamlet may covers its own sub-area of the framed surface area to be scanned. Note that, while a two-dimensional array of beamlets may be used for swath scanning as shown in FIG. 9B, an alternative implementation may use a one-dimensional array of beamlets for swath scanning (where the array of beamlets would extend along the Y-dimension in the figure).

While the illustrated example of a primary beamlet array in FIGS. 9A and 9B show nine beamlets in a 3×3 array, the number of beamlets in the primary beamlet array will depend on the particular implementation. In one embodiment, the number of beamlets in the primary beamlet array may correspond to the number of cells in the detector array. For example, if there are 25 detector cells in a 5×5 array to detect SE beamlets, then there may be 25 primary beamlets in a 5×5 array.

CONCLUSION

The throughput of electron beam inspection systems is mainly limited by the electron-optics and the scanning/imaging strategy. The electron-optics determines the trade off between resolution (related to sensitivity) and beam current (related to speed), where the maximum allowed beam current at certain resolution is limited by lens aberrations, source brightness and electron-electron interactions.

The conventional electron-beam inspection optics is based on a single beam approach. Given the shortest column length, the highest beam energy and the brightest source that can be practically achieved by the state-of-the-art technology, the single-beam based approaches are always constrained to the beam current range that is several orders of magnitude lower than what is required for the high throughput inspection in the semiconductor industry roadmap. For example, the roadmap may require greater than 0.1 wafer per hour throughput for less than 3× design rule layer inspection.

There have been several proposed multi-column and multi-beam approaches attempting to achieve above goal; but none of them is successful so far either due to feasibility issues or an inadequate throughput boost. For example, those previous multi-column based approaches can only offer very limited extension versus a single-beam approach because a maximum of only about 5 to 10 columns can be effectively integrated together, so the throughput boost is less than 10×. Multi-beam (sharing the same column) approaches developed so far are too complicated to be feasible as practical inspection products. For example, most of them need individual beamlet control, deflection and focus, or require novel source technology which is far from mature. In contrast, the present disclosure provides a multi-beam approach that is feasible enough to be implemented as a reliable product within the roadmap required time frame.

The above-described diagrams are not necessarily to scale and are intended be illustrative and not limiting to a particular implementation. In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A multiple-beamlet electron beam imaging apparatus for imaging a surface of a target substrate, the apparatus comprising:
   an electron source configured to emit electrons;
   a condensor electron lens configured to focus the emitted electrons from the electron source into an illumination beam;
   a beam splitter lens array configured to split the illumination beam to form a primary beamlet array, wherein the beam splitter lens array comprises a multiple-layer electrostatic lens array stack;
   an objective electron lens configured to focus the primary beamlet array onto the surface of the target substrate so as to produce a secondary electron beamlet array;
   a scanning system configured to scan the primary beamlet array over an area of the surface of the target substrate; and
   a detection system configured to detect individual secondary electron beamlets of the secondary electron beamlet array.

2. The apparatus of claim 1, further comprising:
   transfer electron-optics arranged between the beam splitter lens array and the objective electron lens.

3. The apparatus of claim 2, wherein the transfer electron-optics is configured to focus the primary beamlet array onto a back-focal plane of the objective electron lens.

4. The apparatus of claim 2, wherein the scanning system includes a pre-scanner arranged above the transfer electron-optics and a main scanner arranged below the transfer electron-optics.

5. The apparatus of claim 1, wherein the detection system includes secondary electron adjustment optics.

6. The apparatus of claim 5, wherein the secondary electron adjustment optics includes a focus adjustment electron lens, a rotation adjustment electron lens, and a magnification adjustment electron lens.

7. The apparatus of claim 6, wherein the secondary electron adjustment optics further includes an array of detector cells.

8. The apparatus of claim 7, wherein the array of detector cells has a number of cells which is equal to a number of secondary electron beamlets in the secondary electron beamlet array.

9. The apparatus of claim 1, wherein the electrostatic lens array stack comprises alternating electrically-grounded and electrically-floating electrode plates.

10. The apparatus of claim 9, wherein said electrode plates are perforated with a plurality of beamlet-forming columnar openings which are aligned from plate to plate so as to extend through the electrostatic lens array stack.

11. The apparatus of claim 1, wherein the objective electron lens is configured to focus the primary beamlet array such that the primary beamlet array lands normal to the surface of the target substrate.

12. The apparatus of claim 1, wherein the scanning system is configured to scan each primary beamlet of the primary beamlet array in a raster pattern such that said primary beamlet covers a corresponding sub-area of a framed surface area.

13. The apparatus of claim 1, further comprising a translatable stage which holds the target substrate, wherein the scanning system is configured to scan each primary beamlet of the primary beamlet array in a first dimension while the target substrate is translated under the primary beamlet array in a second dimension which is perpendicular to the first dimension.

14. A method of imaging a surface of a target substrate using a multiple-beamlet electron beam column, the method comprising:
   emitting electrons into a vacuum chamber;
   focusing the emitted electrons from the electron source into an illumination beam;
   splitting the illumination beam using a multiple-layer electrostatic lens array stack to form a primary beamlet array;
   focusing the primary beamlet array onto the surface of the target substrate using an objective electron-lens so as to produce a secondary electron beamlet array;
   scanning the primary beamlet array over an area of the surface of the target substrate; and
   detecting individual secondary electron beamlets of the secondary electron beamlet array.

15. The method of claim 14, further comprising:
   focusing the primary beamlet array onto a back-focal plane of the objective electron lens using transfer electron-optics.

16. The method of claim 14, further comprising adjusting the focus, rotation, and magnification of the secondary electron beamlet array prior to detecting the individual secondary electron beamlets.

17. The method of claim 14, wherein each primary beamlet of the primary beamlet array is scanned in a raster pattern such that said primary beamlet covers a corresponding sub-area of a framed surface area.

18. The method of claim 14, wherein each primary beamlet of the primary beamlet array is scanned in a first dimension while the target substrate is translated under the primary beamlet array in a second dimension which is perpendicular to the first dimension.

19. An automated inspection system for inspecting a surface of a target substrate using a multiple-beamlet electron beam column, the automated inspection system comprising:
   an electron source configured to emit electrons;
   a condensor electron lens configured to focus the emitted electrons from the electron source into an illumination beam;
   a beam splitter lens array configured to split the illumination beam to form a primary beamlet array, wherein the beam splitter lens array comprises a multiple-layer electrostatic lens array stack;

an objective electron lens configured to focus the primary beamlet array onto the surface of the target substrate so as to produce a secondary electron beamlet array;

a scanning system configured to scan the primary beamlet array over an area of the surface of the target substrate; and a detection system configured to detect individual secondary electron beamlets of the secondary electron beamlet array.

* * * * *